United States Patent [19]

Iizuka

[11] Patent Number: 4,629,627

[45] Date of Patent: Dec. 16, 1986

[54] ANTIVIRAL SUBSTANCE AND THE MANUFACTURING METHOD THEREOF

[76] Inventor: Chiyokichi Iizuka, 121 Shimizu Nodashi, Chibaken, Japan

[21] Appl. No.: 517,328

[22] Filed: Jul. 26, 1983

Related U.S. Application Data

[63] Continuation of Ser. No. 254,657, Apr. 16, 1981, abandoned, which is a continuation-in-part of Ser. No. 109,199, Dec. 27, 1979, abandoned.

[30] Foreign Application Priority Data

Dec. 29, 1978 [JP] Japan ............................ 53-162087

[51] Int. Cl.$^4$ ............................................. A61K 35/78
[52] U.S. Cl. ................................................. 424/195.1
[58] Field of Search ............................ 424/195, 195.1

[56] References Cited

FOREIGN PATENT DOCUMENTS

| 2845765 | 4/1979 | Fed. Rep. of Germany | 424/195 |
|---|---|---|---|
| 0076413 | 6/1977 | Japan | 424/195 |
| 0017188 | 2/1979 | Japan | 424/195 |
| 0047624 | 4/1980 | Japan | 424/195 |
| 1594227 | 7/1981 | United Kingdom . | |

*Primary Examiner*—Leonard Schenkman
*Assistant Examiner*—John W. Rollins
*Attorney, Agent, or Firm*—Abelman Frayne Rezac & Schwab

[57] ABSTRACT

An antiviral substance having, as an active component, a mixture of polysaccharide and cytokinin active substances primarily consisting of zeatin-related substances which are extracted from the nutrient medium and tissue-medium of Basidiomycetes such as *Lentinus edodes* and the manufacturing method thereof, is described.

4 Claims, 5 Drawing Figures

ANTIVIRAL SUBSTANCE AND THE MANUFACTURING METHOD THEREOF

This is a continuation of Ser. No. 254,657, filed Apr. 16, 1981, now abandoned, which is a continuation-in-part application of U.S. patent application Ser. No. 109,199, filed Dec. 27, 1979, now abandoned.

BACKGROUND OF THE INVENTION

The present invention relates to an antiviral substance having, as the active component, a mixture of polysaccharides and cytokinin active substances primarily consisting of zeatin-related substances which are extracted from the nutrient medium and tissue-medium of Basidiomycetes such as *Lentinus edodes* and formulated as it is without fractionating into special fractions, and to a method of treating viral hepatitis.

It is well known that a virus is a filter-passing pathogen, is from $20\mu$ to $60\mu$ in size and smaller than rickettsia, is parasitic in organisms other than viruses, and can proliferate only in living cells.

Viruses are pathogens of such diseases as Japanese encephalitis, influenza and hepatitis in animals, and recently there has been proposed a theory that a virus may be a pathogen of cancer, in an important paper on "Mechanism of carcinogenisis" by Eiichi Soeda, a member of National Genetics Laboratory, appeared in "Nature" an English science magazine, dated Jan. 31, 1980. According to the paper, cancer is induced not by incubation of a carcinogenic virus, but by a hereditarily existing cancerous gene (a normal cell has a cancerous gene, and about 90% of persons may have it,) is excited by X-ray or some chemical substances (carcinogenic substances) to induce cancerous protein resembling mid-sized cancerous protein of a cancerous virus, which relates to carcinogenesis.

The present inventor has researched mycelia of *Lentinus edodes*, and accomplished many inventions as to the method of extracting pharmacologically active components contained in the mycelia, while the present inventor has found out that an active substance of the cytokinin system is contained in the extract of the mycelia and that its extract is effective on vegetable viruses.

The present invention is accomplished by developing the above findings further and it is surely the present inventor who discovered first the presence of cytokinin (zeatin, zeatin ribocide, etc.) in the extract of nutrient medium and tissue-medium of *Lentinus edodes*.

The present invention relates to an antiviral substance prepared by pure-culturing of mycelia of *Lentinus edodes* by solid or deep cultivation, heating or homogenizing them to extract the component of the mycelia and the component of the metobolite simultaneously from the aqueous solvent, and refining the extract by filtering, condensation or freeze-drying, and the manufacturing method thereof.

It has been already known that some polysaccharides have antiviral activities, and some inventions of polysaccharides from Basidiomycetes are partially published; the present inventor has observed the vegetable hormone produced by Basidiomycetes and confirmed it as a cytokinin active substance mainly consisting of a zeatin-related substance; moreover, the inventor has found out that a mixture of the polysaccharide contained in the nutrient medium and tissue-medium of *Lentinus edodes* and the said cytokinin active substance is very effective on viral hepatitis, and thus accomplished the present invention.

The polysaccharide derived from Basidiomycetes which has been studied by some workers is the one which a component of a fruiting body or a mycelium, but the substance produced by a mycelium, i.e., a metabolite is discarded as waste in the extracting process.

The present inventor has observed the substance produced by the said mycelium, which is the metabolite, and a partial decomposition product of lignin by the mycelium as well as the component of the mycelium, and accomplished the present invention.

In the present invention the active component includes not only the component of the mycelium but the component of the metabolite produced by the mycelium and the component contained in the partial decomposition product of lignin, and the present inventor considers the nitrogen-containing polysaccharide in the extract as one of the antiviral components: the polysaccharide is of a rather low molecular weight i.e., from 3000 to 10000. Taking the sugar composition and amino acid composition of the extract, the polysaccharide is not the one in the mycelium but the one in the metabolite produced by the mycelium. In addition, the polysaccharide is quite different from the polysaccharide coming from a fruiting body or mycelium and has structural components different from those of the latter. The partial decomposition product of lignin from the medium will of course have an antiviral activity.

These components seem to act to increase immunity as well as to prevent the viral infection: that is, an antiviral substance has contact with tissue protein to degenerate it and to stop the virus before it causes the disease and inactivate it. In the metabolite, cytokinin active substances of vegetable hormone such as zeatin and zeatin ribocide and the anticytokinin active substance analogous to abscisic acid are confirmed to be present, and they may contribute to control of DNA synthesis.

The antiviral substance of this invention is characterized by being obtained from the extract of the nutrient medium and tissue-medium of *Lentinus edodes* as it is, and is administered without fractionating into special fractions.

SUMMARY OF THE INVENTION

The main purpose of the invention is to propose antiviral substance which are safe and effective for the treatment of virus-induced diseases such as viral hepatitis.

Another purpose of the invention is to propose antiviral substances which are easily manufactured with low cost.

BRIEF DESCRIPTION OF THE DRAWINGS

FIG. 1 is a gasichromatographic figure of the fraction development of a cytokinin active substance of the present invention.

FIG. 2-1 is a gasichromatographic figure showing the peak values of already known cytokinin active substances; basic values are shown in this figure.

FIG. 2-2 is the figure in which the peak of the fraction II in FIG. 1 is developed by gasichromatography.

FIG. 2-3 is the figure in which the peak of the fraction III in FIG. 1 is developed by gasichromatography.

FIG. 3 is the fraction developing figure of the constituting sugar of the present invention by gasichromatography.

DETAILED DESCRIPTION OF THE INVENTION

The substance of this invention is obtained from the metabolite of mycelia and the cellisolution produced by self digestion of mycelia after culturing the mycelia of *Lentinus edodes* in a solid or liquid medium.

*Lentinus edodes* is used as Basidiomycetes in the present invention, and the extract from the mycelium of *Lentinus edodes* shows the highest activity in Basidiomycetes.

Either a solid or liquid medium can be used. As examples of the former, there may be used any one of the bagasse media mainly consisting of bagasse (dregs of sugar cane) developed by the present inventor (bagasse:rice bran, 10:1), the beet medium mainly consisting of beet dregs (beat dregs:rice bran, 12:1), and usually used shavings medium (shavings:rice bran, 3:1). Bagasse has been burnt mostly because no use could be made of it, and thus it is easily and cheaply available. As the latter, there are GPY medium (a synthetic liquid medium consisting of glucose, peptone, and yeast) and MY medium (a synthetic liquid medium consisting of malt extract powder and yeast): it is preferable to add a vegetable fiber component. No particular method is used for culturing the mycelia.

The present invention is characterized by culturing the above-described mycelia of Basidiomycetes in a solid or liquid medium, and extracting the active substance contained in the metabolite of the mycelia and the mycelia from the mixture of the mycelia and the medium (which is called the nutrient medium and tissue-medium in this specification) without separating the mycelia and the medium. Sephadex LH-20 column chromatography of the above-described nutrient medium and tissue-medium reveled six cytokinin active substances, which were identified to be mainly consisting of zeatin and zeatin riboside by gas chromatography, and also showed the presence of polysaccharides.

The present antiviral substance is proved to be effective on diseases caused by viruses such as viral hepatitis, and its toxicity was also found to be extremely low in the safety test. In addition, the substance oral toxicity test of a freeze-dried powder gave the values of 3.84 g/kg/day×90 in male rats and 7.98 g/kg/day×90 in female rats.

EXAMPLE 1

A solid medium consisting of 90% of bagasse, 5% of rice bran and 5% of nutritional material such as bran was sterilized as usual, and solid seed mycelium of *Lentinus edodes* was inoculated on it. The inoculated medium was then put in a culture room kept at a temperature of 18° to 20° C. at a humidity of 60% by air-conditioning and the culture of the mycelium was begun.

When finishing the culture, the medium was transferred into a culture room and allowed to stand there. When fruiting bodies began to grow up from the surface of the medium, the medium was taken out of the culture room, and crushed into thumb sized pieces by a crusher. The crushed medium was packed in a tank to which 5 liters of clean water per 600 grams of the medium were added; then, they were mixed at 60° to 130° C. for 4 to 5 hours with agitation. The active components in the metabolite of the mycelia and the mycelial cell solution were released into the water by agitation.

The resulting suspension was packed in a filtering bag of flannel and compressed to filter: the obtained filtrate was again filtered to remove fungi by a membrane filter and the active substance contained in the metabolite of the mycelium and the mycelial cell solution was extracted. Then, the extract was compressed to condense through an ultrafilteration membrane, and freeze-dried, resulting in a brown powder.

Mycelia of flammulina uelutipes sing, *Pleuratus ostreatus, Coriolur uersicolor* and the like were cultured and the corresponding mycelial extracts were obtained by similar method to the above-described ones, and then cytokinin and polysaccharide were identified.

(1) Separation and purification of cytokinin active substances:

The brown powder obtained by freeze-drying the extract of the nutrient medium and tissue-medium of *Lentinus edodes* was dissolved in the water and allowed to stand at 5° C. overnight, followed by discarding the insoluble part. Then, the filtrate was adjusted at pH 1.5 with HCl and mixed with an equal amount of ethyl acetate; the ethyl acetate transferred substance was removed. The aqueous phase was adjusted at pH 8.7 by adding ammonia, extracted from an equal amount of water-saturated n-butanol; the n-butanol phase was adsorbed by Dowex 50-X 4 (RTM), and a cytokinin active substance was obtained after efflution of ammonia.

The above described active substance was treated through Sephadex LH-20 column chromatography to divide it into six cytokinin active components, which were identified by gas chromatography to be mainly composed of zeatin and zeatin riboside; in yields there was obtained 50 mg of zeatin and zeatin riboside per 1 gram of the powder. The results of Sephadex LH-20 column chromatography and gas chromatography are shown in FIG. 1 and FIG. 2, respectively. The presence and absence of the activity was examined biologically with seed leaves of the radish. As seen in FIG. 1, the cytokinin activity is recognized in the fraction I–IV. FIG. 2-1 is a chart of the already known cytokinin; B, isopentenyl adenine; C, dihydro-zeatin; D, zeatin; E, isopentenyl adenosine, and F, zeatin riboside. FIG. 2-2 is a chart of the fraction II in FIG. 1; as it is coincident with F in FIG. 2-1, it is defined to be zeatin fiboside. FIG. 2-3 is a chart of the fraction III in FIG. 1, and as it is coincident with D in FIG. 2-1, it is defined as zeatin.

The cytokinin active substance in the present invention is a substance which is purified by ion exchange treatment with Dowex 50-X 4, and is a mixture of six cytokinin active components.

(2) Separation and purification of polysaccharide.

The freeze-dried brown powder of *Lentinus edodes* which was similarly prepared as the above one was dissolved in the water, mixed with 10% trichloracetate (10% TCA) added thereto, stirred and centrifuged. To the obtained supernatant 3-fold volume of 95% ethanol was added, stirred and centrifuged. Then, the precipitate was dried, dissolved in the water again, and also dissolved in a 3-fold volume of acetone: the solution was centrifuged and the resulting precipitate was dried.

| Group | Added quantity | Results E. coag. value | Inhibition rate, % |
|---|---|---|---|
| Control | 0 | 132 | — |
| Cytokinin | 0.2 PPM | 36 | 72.7 |
| Polysaccharide | 0.5 PPM | 14 | 89.4 |

| Group | Added quantity | E. coag. value | Inhibition rate, % |
|---|---|---|---|
| Cytokinin + Polysaccharide | 0.2 PPM + 0.5 PPM | 2 | 98.5 |

In each treated group the viral inhibition rate was high, but the highest was in the cytokinin+polysaccharide group. In the group containing cytokinin the proliferation rate of cells tended to be higher than that in the control group.

EXPERIMENT 2

Protective activity of mice to herpes virus: Based on the result of Experiment 1 the effect of cytokinin+polysaccharide was found to be excellent, and the treatment was performed with a mixture of cytokinin and polysaccharide.

The mixture of cytokinin and polysaccharide was given intraperitoneally to 2-week old mice, and the survival rate was obtained after 14 days.

Inoculated amount of the virus: $2 \times 10^3$ PFU

Dose of the mixture: 2 mg of cytokinin and 5 mg of polysaccharide

A group consisting of 10 mice: the test was repeated 5 times

Survival rate: mice/10 groups

| Group | Surv. rate | |
|---|---|---|
| 1. Group given only herpes virus | 0 | 1 |
| 2. Group given herpes virus, cytokinin and polysaccharide | 7 | 10 |
| 3. Group inoculated with the virus 48 hours after giving cytokinin and polysaccharide | 9 | 10 |
| 4. Group given cytokinin and polysaccharide 48 hours after inoculation of the virus | 6 | 8 |

Treatment with cytokinin and polysaccharide could well prevent the viral infection, and also showed satisfactory thereapeutic effects.

EXPERIMENT 3

The present inventor asked Prof. Nobuhiko Kanno, Biological Laboratory, Dept. of Pharmacology, Toyama Medical and Pharmacologival University, to test the activity of the present antiviral substance to depress the liver cancer in rats on pathogens of viruses.

Method

1. Test animals: Wister male rats of 4 weeks of age were fed for 5 days as usual and tested.
2. Carcinogenic substance: 3'-methyl-4-dimethyl amino azobenzene (3'-Me-DAB)

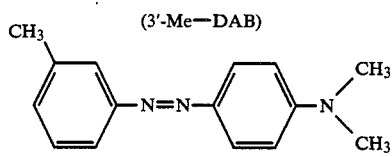

(3'-Me—DAB)

3'-Me-DAB is known to have an affinity to a rat's liver and has a specific and strong carcinogenic property. The carcinogenic process is reported as showing that 3'-Me-DAB is connected with the protein of liver cytoplasm to initiate formation of liver cancer.

3. Test group:
   (1) Control group: standard food
   (2) L group: standard food+L
   (3) L+DAB group 0.06% 3'-Me-DAB containing food+L
   (4) DAB group 0.06% 3'-Me-DAB containing food
   Note: L: a frozen dry powder of the extract of the nutrient medium and tissue-medium of *Lentinus edodes* DAB: 3'-Me-DAB 4. Quantity and the method of giving the freeze-dried powder of the extract of the nutrient medium and tissue-medium of *Lentinus edodes*

| Period (day) | Interval (day) | Dose | Concentration (w/v) |
|---|---|---|---|
| 0 20 | 2 | 1.0 g/Kg | 20% |
| 21 41 | 3 | 150 mg/body | 20% |
| 42 100 | 3 | 50 mg/body | 6.67% |
| 101 | 5 | 50 mg/body | 6.67% |

The freeze-dried powder of the nutrient medium and tissue-medium of *Lentinus edodes* was dissolved in physiological salt water, and given intraperitoneally; the same dose of physiological salt water was similarly given to the control group.

5. Process and results:
(1) Microscopic observation: Within about 5 weeks, depilation appeared on the abdomen in some a rats of the DAB group, and gradually spread and the degree of the depilation also progressed.

Within about 15 weeks, some rats began to show depilation on the neck or the side of the body. No depilation appeared in the L+DAB group.

(2) Autopsy: In the dissection of the DAB group after 14 weeks and 18 weeks, fine yellowish white particles which seemed to be cancerous tissue were seen all over the liver. In the L+DAB group, the liver showed no apparent abnormal finding. All of the rats which showed some abnormal findings in the liver were those which had depilation.

(3) Microscopic findings of the liver tissue: The liver tissue was stained by hematoxin-eosin, fixed in wax and prepared into 8μ thick section to examine microscopically.

The liver tissue of the DAB group in which yellowish white particles appeared showed severe disarrangement of cells and the glandular structure specific to liver cancer (adeno carcinoma); the nucleolus was clearly stained by eosin and was enlarged; cancerous cells were obviously seen. In the liver tissue in the L+DAB group, the cell arrangement was slightly disturbed, but adeno carcinoma was not seen nor changes of the muleolus was not; thus they were judged normal cells.

Based on the above results, the freeze-dried powder of the nutrient medium and tissue-medium of *Lentinus edodes* cleary inhibited the carcinogenic activity of 3'-Me-DAB on rats, and has antiviral activity.

(4) Six grams of the brown powder obtained by the method described in Example 1 were solved in 100 c.c. of water and given to a patient with viral hepatitis once a day before breakfast every day, and the following therapeutic effects were obtained.

Case 1: a female patient, 50 years old, who was a head nurse of a hospital and was diagnosed as having epidemic hepatitis.

The serum transaminase activity was determined to obtain the therapeutic results, which are shown below. The normal value: GOT, 8–40; GPT, 5–35; Kunkel, 4–12.

Case 2:

The present inventor asked Nishitetsu Hospital (Fukuoka, Fukuoka Pref.) to test the present substance, which was given to a patient with epidemic viral hepatitis to produce the following results. The freeze-dried powder began to be given orally with a dose of 5 grams on Sept. 25.

| Item | | | | 8/27 | 9/10 | 9/17 | 9/27 | 10/8 | 10/15 | 10/22 | 11/5 | 11/12 | 11/26 |
|---|---|---|---|---|---|---|---|---|---|---|---|---|---|
| Jaundice index (MG) | | | | 5 | 5 | 5 | 4 | 5 | 4 | 5 | 5 | 7 | 6 |
| Serum | GOT | | | 46 | 43 | 33 | 44 | 50 | 65 | 90 | 119 | 113 | 143 |
| transaminase | GPT | | | 46 | 40 | 44 | 40 | 42 | 54 | 73 | 115 | 90 | 99 |
| Serum | Cobalt reaction | | | | | | | | | | | | |
| colloidal | T.T.T. | | | 7.1 | 6.0 | 6.9 | 6.4 | 7.5 | 7.8 | 7.9 | 9.1 | 8.7 | 8.7 |
| reaction | Zn T.T. | | | 8.0 | 9.5 | 8.5 | 8.3 | 9.4 | 8.6 | 8.7 | 10.4 | 10.3 | 11.6 |
| Serum | Total protein | | | 7.8 | 7.7 | 7.3 | 7.3 | 8.1 | 7.9 | 7.7 | 7.8 | 7.6 | 7.9 |
| protein | Protein | Albumin | | 65.6 | 67.9 | 67.1 | 67.1 | 63.9 | 68.4 | 66.2 | 66.0 | 65.7 | 64.9 |
| | fraction | Globulin | $\alpha_1$ | 3.1 | 3.0 | 3.0 | 3.3 | 3.5 | 3.2 | 3.1 | 3.4 | 3.3 | 3.4 |
| | ratio | | $\alpha_2$ | 9.3 | 9.2 | 9.1 | 8.6 | 9.4 | 9.2 | 8.8 | 7.9 | 8.7 | 8.5 |
| | | | $\beta$ | 7.1 | 7.9 | 7.1 | 7.3 | 8.0 | 7.1 | 7.3 | 8.0 | 7.5 | 7.3 |
| | | | $\gamma$ | 14.6 | 11.7 | 13.5 | 13.5 | 14.9 | 11.9 | 14.3 | 15.6 | 14.6 | 15.7 |
| | A/G | | | 1.91 | 2.11 | 2.04 | 2.04 | 1.77 | 2.161 | 1.96 | 1.94 | 1.91 | 1.84 |
| | Al - P | | | 11.0 | 9.6 | 10.3 | 10.7 | 11.7 | 10.6 | 10.2 | 9.2 | 11.7 | 11.4 |
| Total cholesterol | | | | 193 | 188 | 185 | 191 | 195 | 203 | 173 | 201 | 188 | 195 |
| L.D.H. | | | | | | | | | | | | | |
| LAP | | | | 215 | 203 | 185 | 186 | 193 | 210 | 215 | 215 | 219 | 257 |
| γ-GPT | | | | 24.9 | 23.7 | 22.8 | 21.7 | 26.2 | 24.84 | 24.0 | 31.5 | 30.5 | 33.7 |
| α-FP | | | | (+) | (−) | (−) | (−) | (−) | (−) | (−) | (−) | (−) | — |
| HB$_s$ antigen | | | | (+) | (+) | (+) | (+) | (+) | (−) | (−) | (−) | (−) | — |

| | | | | 1979 | | | | 1980 | | | | |
|---|---|---|---|---|---|---|---|---|---|---|---|---|
| Items | | | | 12/3 | 12/10 | 12/17 | 12/24 | 1/7 | 1/21 | 1/28 | 2/4 | 2/18 |
| Jaundice index (MG) | | | | 6 | 7 | 6 | 7 | 5 | 6 | 6 | 5 | 6 |
| Serum | GOT | | | 110 | 136 | 104 | 67 | 57 | 38 | 38 | 35 | 34 |
| transaminase | GPT | | | 91 | 105 | 71 | 64 | 48 | 35 | 30 | 28 | 26 |
| Serum | Cobalt reaction | | | | | | | | | | | |
| Colloidal | T.T.T. | | | 9.4 | 9.6 | 9.1 | 9.4 | 9.9 | 9.1 | 8.0 | 9.1 | 7.9 |
| reaction | Zn.T.T. | | | 12.2 | 12.7 | 11.9 | 12.4 | 11.9 | 11.1 | 10.6 | 11.2 | 9.7 |
| Serum | Total protein | | | 7.9 | 8.1 | 7.6 | 7.9 | 8.0 | 8.1 | 7.4 | 8.1 | 7.9 |
| protein | Protein | Albumin | | 63.7 | 63.9 | 63.1 | 64.8 | 63.8 | 61.8 | 65.6 | 63.5 | 64.9 |
| | fraction | Globulin | $\alpha_1$ | 2.6 | 3.9 | 3.2 | 2.9 | 3.8 | 3.9 | 3.2 | 2.9 | 3.5 |
| | | | $\alpha_2$ | 7.9 | 8.7 | 8.2 | 7.6 | 9.0 | 9.1 | 8.4 | 9.8 | 9.2 |
| | | | $\beta$ | 7.4 | 7.3 | 7.6 | 7.7 | 7.7 | 8.7 | 8.0 | 8.2 | 9.2 |
| | | | $\gamma$ | 18.2 | 16.0 | 17.6 | 16.7 | 15.4 | 16.3 | 14.5 | 15.3 | 14.1 |
| | A/G | | | 1.75 | 1.77 | 1.71 | 1.84 | 1.76 | 1.61 | 1.91 | 1.74 | 1.85 |
| | Al - P | | | 14.2 | 10.4 | 13.4 | 10.6 | 15.5 | 13.2 | 10.2 | 14.5 | 9.7 |
| Total cholesterol | | | | 194 | 208 | 189 | 197 | 209 | 206 | 177 | 191 | 221 |
| L.D.H. | | | | | | | | | | | | |
| LAP | | | | 250 | 228 | 219 | 245 | 223 | 193 | 180 | 199 | 183 |
| γ-GPT | | | | 37.3 | 37.4 | 36.3 | 37.7 | 33.6 | 29.2 | 26.1 | 27.1 | 23.4 |
| α-FP | | | | — | (−) | — | — | — | — | — | (−) | (−) |
| HB$_s$ antigen | | | | — | (−) | — | — | — | — | — | (−) | (−) |

(a) at the onset on May 12, 1978, GOT, 170; GPT, 270; Kunkel, 5

(b) on hospitalization on June 7, 1978, GOT, 756; GPT, 793; Kunkel, 7

(c) the administration of a daiy dose of the mixture starting on July 15, 1978, as described above (d) on determination on June 21, 1978, GOT, 230; GPT, 320; Kunkel, 7

(e) on determination on July 6, 1978, GOT, 140; GPT, 230; Kunkel, 7

(f) on determination on Aug. 1, 1978, GOT, 22; GPT, 19; Kunkel, 7

(g) She was completely cured and discharged on Aug. 2, 1978, and returned on her work on the same day.

(h) on determination on Aug. 19, 1978, GOT, 27; GPT, 25; Kunkel, 7

A dose of 5 grams of the freeze-dried powder was given orally every day, and as seen in the above results, the HBs antigen test turned to negative after about 20 days, and then the patient cured completely.

The present inventor asked Nagahama Red Cross Hospital (Nagahama, Siga Pref.) to test the present substance; it was given to a patient with acute viral hepatitis (Case 3) and a patient with severe epidemic hepatitis (Case 4) and the following results were obtained.

| Case 3: (Patient with acute epidemic hepatitis) | | | | |
|---|---|---|---|---|
| Name | Date | AlP | GOT | GPT | LDH |
| a 42 years old male, who was discharged in the early March | | | | |
| OM | 1/17 | 27.5 | 561 | 522 | 876 |
| | 1/25 | Oral administration of a dose of 5 grams of a freeze-dried powder of an extract of the nutrient medium and tissue-medium of Lentinus edodes was | | | |

Case 3: (Patient with acute epidemic hepatitis)

Name: a 42 years old male, who was discharged in the early March begun.

| Date | AIP | GOT | GPT | LDH |
|---|---|---|---|---|
| 1/28 | 26.0 | 533 | 471 | 780 |
| 2/4 | 22.7 | 96 | 122 | 362 |
| 2/11 | 21.1 | 79 | 90 | 477 |
| 2/18 | 16.7 | 89 | 93 | 435 |
| 2/25 | 13.5 | 80 | 64 | 358 |
| 3/3 | 13.8 | 38 | 38 | 340 |

Case 4: (Patient with severe epidemic hepatitis)

| Name | Date | AIP | GOT | GPT | LDH |
|---|---|---|---|---|---|
| E M | 1/16 | 19.1 | 4550 | 3730 | 3832 |
|  | 1/19 | 18.6 | 4420 | 3690 | 3660 |
|  | 1/25 | Oral administration of a dose of 5 grams of a freeze-dried powder of an extract of the nutrient medium and tissue-medium of Lentinus edodes was begun. | | | |
|  | 1/26 | 18.9 | 3460 | 3720 | 3560 |
|  | 2/2 | 13.8 | 391 | 471 | 604 |
|  | 2/9 | 15.0 | 380 | 129 | 352 |
|  | 2/16 | 19.2 | 43 | 73 | 311 |
|  | 2/23 | 14.9 | 36 | 40 | 278 |
|  | 3/1 | 11.9 | 25 | 31 | 270 |
|  | 3/8 | 10.1 | 28 | 29 | 292 | a 45 year old male in hospital

As clearly seen in the above cases, after administration of several does of the drugs, GOT and GPT both decreased, and particularly in the patient with severe viral hepatitis who was in dangerous condition when being hospitalized, both values decreased within several days. Now, both of the patients have been completely cured, indicating an astonishingly high therapeutic effect of the substance.

Case 5: a 74 year old male of serum hepatitis

In March in 1979 he was attacked by cerebral infarct and then by deglutive hepatitis, and was subjected to tracheotomy on September 20. Because the oral excretion was heavy and could not be removed, nasal feeding was begun from Sept. 29. Anemia occurred due to shortage of calories, and the blood was often transfused, Then, the values of GOT 30, GPT 26.5 and Al-P.7.0 in September of 1979 increased to 62, 133 and 34.2 on Dec. 3, respectively; he began to vomit on every nasal feeding (800 cal. of fruit juice plus tang. juice, etc) though he had not vomited before; the liquid transfusion was then increased to 1500 ml (daily) and the condition became intractable. Then, a daily dose of 5 grams of the freeze-dried powder of the nutrient medium and tissue-medium of Lentinus edodes was dissolved in water and given through the nose from December 19 to February 18. On December 21, the laboratory test results were improved at TTT 1.8, ZnTT 9.1, GOT 39, GPT 45.5 and Al-P 17, and simultaneously vomiting disappeared, and the general conditions were gradually improved. On January 16, the values were GOT 28, GPT 22, and Al-P 14, and on February 13, they were GOT 26, GPT 14, and Al-P 12: then, they increased and the subjective symptoms disappeared.

Case 6: a 73 year old male of serum hepatitis

Past anamnesis: In September 1944, he was diagnosed as having rectal cancer and subjected to the surgical operation of artificial anus in 1945. On Aug. 28, 1978, he was attacked by cerebral infarct and admitted to Miyake Hospital, Toshincho, Omuta, Fukuoka Pref.. On Jan. 25, 1979, he had a complication of cancerous peritonitis, (with intestinal paralysis), but recovered without surgical treatment. Additionally, he had an intractable uninary infection and senile cutaneous pruritus, and in October in 1979 he had acute pneumonia. He was blood-transfused because of anemia, and soon the CRP became 5+; On Nov. 19 in 1979, there were obtained values of TTT 4.7, ZnTT 8.9, GOT 192, GPT 230, $\beta$-TP 7.08/dl, A/G 0.55% and gamma-globuin 40.00%. The T cells were 847/1,284=64%. A daily dose of 5 grams of the freeze-dried powder of the nutrient medium and tissue-medium of Lentinus edodes was given for 2 months from Nov. 30, 1979. The test results were T cells 847/1,284=64% on November 21, T cells 590/1,311=45% on December 12, TTT 6.5, ZnTT19.8, GOT21.5, GPT 21.5, gamma-globulin 36.33% and A/G 0.64 on December 18. Dysorexia of a subjective symptom disappeared, and he could take much food orally. He showed values of TTT 3.9, ZnTT 20, GOT 17.0, GPT 10, A/G=0.67, gamma-globulin 33.33%, and T cells 773/1,120=69% on January 22, and TTT 4.2, ZnTT 18, GOT 18.5, and GPT 9.5 on February 19. Then, he showed no further exaggeration and did not complain about subjective symptoms particularly. The patient was being given 2 tablets of KW every other week, which caused such general conditions described above and the increase of GOT and GPT; he could be recovered from a dangerous state caused by poor general conditions.

EXAMPLE 2

A GPT medium was mixed with a boiled bagasses solution and packed in a container and sterilized in an autoclave at 121° C. for 30 minutes. A platinum loop of seed hyphae of Lentinus edodes was inoculated on the said medium, mixed by a shaker 120 times per minute in a culture room at 25° C., and subject to deep culture for 7 to 8 days. Then, the mycelia grew in the medium to be like a pellet, indicating the mycelia had grown well.

One liter of the nutrient medium and tissue-medium obtained as described above was homogenized and the resulting suspension was filtered and extracted. The extract was then filtered to condense through an ultrafilter membrane to get an extract, and the resulting extract was freeze-dried to obtain a brown powder. The yield was 10 grams of the brown powder per liter of the extract.

From the material obtained as described above, the cytokinin active substance and polysaccharide were separated and purified as described in Example 1, and then it was identified that zeatin and zeatin riboside of the cytokinin system were contained in the said material.

The antiviral effect of the material obtained as described above was determined similiarly as in Example 1, and almost similar results were obtained.

The present inventor examined the antiviral effect of the powder obtained as described above, and got excellent therapeutic results.

Tumoral cells of sarcoma 180 were transplanted into the abdomen of a mouse, and when they sufficiently proliferated after 8 days, $10^7$ of the cells were transplanted subcutaneously in the lower arm of another mouse to produce a solid tumor; from 24 hours after tansplantation the above-described powder was given to the mouse. It was given intraperitoneally with a dose 10 mg/kg, i.e., 0.2 mg/20 g (the body weight of the mouse) once a day 12 times every other day; orally it was given with a dose of 10 mg/kg, i.e., o.2 mg/20 g (the body weight of the mouse) once a day 23 times every day.

As the result, the antiviral substance (the brown powder described above) of the present invention was found to have an excellent antiviral activity, and to be effective as an antiviral hepatitis drug.

Case 1: a 65 year old male, who was diagnosed as having esophageal cancer (a) 1974: subjective symptoms: smarting on drinking cold fluids. He received the above-described brown powder of the present invention from some of our patients and took it once a day before breakfast with a dose of 3 grams.

(b) December, 1976: He was subjected to X-ray examination in a clinic for confirming his diagnosis and got some findings in the esophagus. Immediately he was examined endoscopically in Tokyo Women's Medical College and was diagnosed as having espohageal cancer because typical cells were found in the esophagus.

(c) February, 1977: He refused a surgical operation: he had a weight of 38 kg, a length of 152 cm and complained of severe fatigue with dullness and loss of appetite.

(d) February, 1977: A lesion was found to be restricted in the regenerated epithelial cells by endoscopic examination.

(e) December, 1977: The appetite abruptly reduced and the patient and his family were very anxious about it.

(f) January, 1978: A dose of the brown powder was increased to 6 grams once a day. The patients appetite was improved 1 week afterwards.

(g) March, 1978: He was improved and showed an increase of body weight.

(i) September, 1978: X-ray and endoscopic examination revealed no abnormal finding in the esophagus.

Case 2: a 45 year old male (a) April, 1977: He was attacked by severe pain in the left abdomen, found to have two masses of fist size, and diagnosed as having a malignant migrating cancer and pancreatic cancer based on X-ray, blood and urine examinations.

(b) May, 1977: a Dose of 6 grams of the above-described brown powder of the present invention was given once a day before breakfast every day.

(c) June, 1977: Several days after the beginning of the administration, the flatus was released to soothe the compressive feeling and the malaise in the left abodomen. Only the powder of this invention was given and the other drugs were ceased. He had bowel movements and felt better.

(d) July, 1977: He felt no pain but malaise in the abdomen, and sometimes had prickling. He was told not to be anxious about it because it was due to beginning of the movements of the duodenum and small intestine. He had grumbling and flatus frequently. The blood, X-ray and other examinations indicated the cure of cancer. After vomiting, much flatus was released every day; the cause of vomiting was considered to be in the intestine.

(e) August, 1977: He was surgically operated, and suppuration of the diaphragm was found. The pus was discharged by suction through the tube every day. The administration of the powder which had been stopped for a while before and after the operation was begun.

(f) September, 1977: He began to feel starved and was able to walk.

(g) October, 1977: He was discharged and visited the hospital as an out-patient. Then, he was completely cured and since then he was not visited the hospital.

EXAMPLE 3

The mycelium of flammulina uelutipes sing were cultured as described in Example 1, and an extract containing the above-described active component was obtained from the nutrient medium and tissue-medium similarly, filtered to condense, and freeze-dried to produce a powder.

The material obtained as described above was examined for antiviral activity and for antitumoral activity, and gave results almost similar to those in the previous examples.

EXAMPLE 4

Pleliata nameko was cultured as described in Example 1, and an extract containing the above-described active component was obtained from the nutrient medium and tissue-medium similarly, filtered to condense, and freeze-dried to produce a powder.

The material obtained as described above was tested for antiviral and antitumoral activities, and gave results similar to those in the previous examples.

Safety of the antiviral substance of this invention:

The antiviral substance produced according to Example 1 was analyzed by Nomura Consolidated Laboratory for evaluating the safety: the results are as follows:

| (1) Acute toxicity (oral) | $LD_{50}$ g/kg (body weight) |
|---|---|
| Rats (male) | 16.5 |
| Rats (female) | 15.6 |
| Mice (male) | 19.6 |
| Mice (female) | 17.7 |
| (2) Toxicity on fish | TLM |
| Carps, 48 hours | ca 1.02% |
| Carps, 72 hours | 1.07% |
| Water flea, 3 hours | 0.56% |

Results: TLM corresponds to $LD_{50}$ for acute toxicity (rats and mice).

Usual synthetic fertilizers show 10 ppm in carps and also show values ppb levels in water flea: thus, the present antiviral substance is confirmed to show extremely low toxicity.

What we claim is:

1. A method of treating viral hepatitis which comprises orally administering to patients having viral hepatitis an antiviral effective amount of a mixture of nitrogen-containing polysaccharides of 3,000 to 10,000 molecular weight and cytokinin, primarily consisting of zeatin-related substances as obtained from the nutrient medium and tissue medium of *Lentinus edodes.*

2. A pharmaceutical composition for treating viral hepatitis which comprises, as active ingredients an antiviral effective amount of a mixture of nitrogen-containing polysaccharides of 3,000 to 10,000 molecular weight and cytokinin, primarily consisting of zeatin-related substances, as obtained from the nutrient medium and tissue medium of *Lentinus edodes.*

3. A composition according to claim 2 wherein the active ingredients are in powder form.

4. A process for preparing a composition for treating viral hepatitis comprising an antiviral effective amount of active ingredients containing a mixture of nitrogen-containing polysaccharides of 3,000 to 10,000 molecular weight and cytokinin, primarily consisting of zeatin-related substances as obtained from the nutrient medium and tissue medium of *Lentinus edodes,* comprising the steps of culturing the *Lentinus edodes* mycelia in a solid or liquid medium, wherein said solid medium comprises bagasse and rice bran in a ratio of about 10:1, or beet dregs and bran in a ratio of 12:1; and wherein said liquid medium comprises glucose, peptone and yeast; and containing a vegetable fiber component, filtering and extracting the active ingredient from the mycelia and freeze drying the extract.

* * * * *